United States Patent
Igel

(10) Patent No.: US 6,413,440 B1
(45) Date of Patent: Jul. 2, 2002

(54) PROCESS FOR MANUFACTURING A MICRO-ELECTRODE

(75) Inventor: Günter Igel, Teningen (DE)

(73) Assignee: Micronas GmbH, Freiburg (DE)

( * ) Notice: Subject to any disclaimer, the term of this patent is extended or adjusted under 35 U.S.C. 154(b) by 0 days.

(21) Appl. No.: 09/351,394

(22) Filed: Jul. 13, 1999

(30) Foreign Application Priority Data

Jul. 14, 1998 (DE) .......................... 198 31 529

(51) Int. Cl.[7] .......................... B44C 1/22; H01L 21/302
(52) U.S. Cl. .................. 216/99; 204/157.15; 204/471; 204/478; 204/479; 205/123; 205/157; 205/91; 205/92; 205/131
(58) Field of Search ............ 204/157.15, 471, 204/478, 479; 205/123, 157, 91, 92, 131; 216/99

(56) References Cited

U.S. PATENT DOCUMENTS

| 5,118,403 A | | 6/1992 | Magee, Jr. et al. |
| 5,660,699 A | * | 8/1997 | Saito et al. .................. 204/297 |
| 5,707,502 A | | 1/1998 | McCaffrey et al. |
| 6,032,062 A | | 2/2000 | Nisch |

FOREIGN PATENT DOCUMENTS

| DE | 41 30 135 A 1 | 3/1993 |
| DE | 42 44 338 A 1 | 7/1994 |
| DE | 44 22 049 A 1 | 1/1996 |
| DE | 195 29 371 A 1 | 2/1997 |
| DE | 44 22 049 C2 | 12/1997 |
| DE | 195 29 371 C2 | 1/1998 |
| EP | 0 653 629 A2 | 5/1995 |
| EP | 0 689 051 A2 | 12/1995 |
| JP | 08-262042 | * 10/1996 |
| WO | WO 97/38301 | 10/1997 |

* cited by examiner

Primary Examiner—George Goudreau
(74) Attorney, Agent, or Firm—Akin, Gump, Strauss, Hauer & Feld, L.L.P.

(57) ABSTRACT

In a process for manufacturing an electrode (1) on a substrate (2) using a conventional structuring process, an electrically conducting surface structure is created which has at least one tip (3) or edge (4). In the area of the tip (3) or edge (4), an electrode layer (5) is galvanized onto the substrate (2) and/or applied by electrostatic powder coating. Then, a surface area of the substrate (2), which surrounds the electrode layer (5) located on the tip (3) or edge (4), is converted into an insulating layer (8) by a chemical reaction. The electrode layer (5) can also be applied in a manner where, in the area of the tip (3) or edge (4), a chemical is released, which upon irradiation by electromagnetic and/or particle radiation, precipitates an electrically conducting material. This chemical is then impinged in the area of the tip (3) or edge (4) with optical radiation.

17 Claims, 5 Drawing Sheets

PROCESS FOR MANUFACTURING A MICRO-ELECTRODE

BACKGROUND OF THE INVENTION

The invention involves a process for manufacturing an electrode, in which a surface structure, with at least one electrically conducting projection having at least a tip or edge, is produced on a substrate.

A process of this type is already known from German published patent application DE 44 22 049 A1. There, a three-dimensional surface structure is first created on a silicon substrate using an anisotropic or isotropic etching process. The surface structure has a number of pyramidal or cone-shaped projections arranged adjacent to each other, each of which has a tip. Then, the substrate is dipped into a polymer solution, or a polymer solution is sprayed onto or poured onto the substrate. On the tips of the projections a film outline thereby occurs which is controlled, in that the surface structure having the projections is exposed to the vapor of a solvent. By the film outline, it should be achieved that the tips remain for the most part free of the polymer solution, while the surface areas surrounding the tips of the projections are covered with the polymer solution, which forms an electrically insulating layer after curing.

The previously known process, however, has proven to be problematic in practice, since the film outline is a statistical process, which does not always progress the same way in the individual projections of the substrate. In particular, different flow behavior of the polymer solution can occur on the individual projections of the surface structure. In addition, it is unfavorable that the polymer solution contains a solvent which is released during the curing of the lacquer layer. Also, the lacquer layer can contain toxic materials, which is especially disadvantageous when the electrodes manufactured according to the process are to be used to examine living biological cells, which react very sensitively to toxic materials. An influencing of the cells can also occur thereby, and thus lead to measurement errors. Moreover, it is disadvantageous that by having the lacquer layer arranged in the intermediate spaces located between the pyramidal or cone-shaped projections, the height of the projections, i.e. the distance between the furthest projecting position of a projection and the furthest set back position of the lacquer layer adjacent to it, is reduced. The electrode area located on the tip of the projection cannot be positioned very well by this, for example, through a cell membrane to the interior of the cell, in order to examine it with the electrode tip. Also, the electrode tip can only be poorly stuck into another soft material to be investigated.

SUMMARY OF THE INVENTION

Therefore, an object of the invention is to create a process of the type mentioned at the beginning, with which a micro-electrode having on its surface an electrically conducting tip or edge surrounded by an electrically insulating surface area can be manufactured while avoiding a lacquer layer that remains in the area of the tip or edge.

The solution of this object consists in that a supply channel is made in the substrate, which opens in close proximity to the tip or edge that is to be mounted on the surface of the substrate, and that through the supply channel a chemical is supplied which emerges at the tip or edge, and which upon irradiation with electromagnetic and/or particle radiation precipitates an electrically conducting material, in particular a metal, and that the chemical is irradiated with electromagnetic and/or particle radiation in the area of the tip or edge in order to precipitate the electrically conducting material at the tip or edge.

The tip or edge can, for example, be created using a traditional structuring process such as anisotropic etching, underetching of a lacquer layer or vapor deposition of the substrate surface through an opening located in a mask arranged near the substrate surface. Through the supply channel the chemical preferably reaches the area of the tip or edge of the substrate, so that the electrically conducting material precipitated out of the chemical with the aid of the electromagnetic and/or particle radiation preferably is deposited there. By an electromagnetic and/or particle radiation is understood here a radiation that supplies energy to the chemical, for example optical radiation, such as light, infrared or ultraviolet radiation, X-ray radiation, or particle radiation, such as alpha, beta or gamma radiation.

Expediently, the supply speed of the chemical emerging in the area of the tip or edge is selected such that it is disposed in the area of the tip or edge during the entire switched-off period of the electrically conducting material. In this way, a possible precipitation of the conducting material outside of the area of the tip or edge is prevented. The electrode manufactured according to the process is thus only conducting on the part of its surface that is located in the area of the tip or edge, while the remaining surface areas are electrically insulating. This can be achieved, for example, in that as a substrate an electrical insulator is used or that an electrically conducting substrate is provided with an insulating surface layer before the switch-off of the electrode material. On the whole, a partially conducting electrode having a micro-electrode tip or edge, which allows a locationally resolved measurement of electric signals, thus results while avoiding a lacquer mask surrounding the electrode layer. The electrode is suitable especially for an examination or treatment of biological cells deposited on the surface of the electrode. The supply channel can, for example, be applied by laser drilling or plasma etching into the substrate. Optionally, the penetration of the supply channel can be done from the rear side of the substrate, which faces away from the tip or edge. For this purpose, for example, an etch-resistant mask can be applied on the rear side of the substrate.

An advantageous embodiment of the process provides that the electromagnetic and/or particle radiation is beamed through the supply channel into the area of the tip or edge. For this purpose, for example, on the end of the supply channel that faces away from the tip or edge, a laser beam can be coupled into the supply channel. The optical radiation can thereby be positioned in a simple way on the tip or edge. Since the electromagnetic and/or particle radiation becomes interspersed in the chemical located in the supply channel, the electrically conducting material is also precipitated out in the supply channel and can deposit on its wall. The wall of the supply channel then forms an electrically conducting bond to the electrode tip or edge. In the electrode manufactured according to the process, an electrical voltage can, for example, be applied via this bond conductor to the electrode tip, or a measurement signal on the electrode tip can be measured. In an advantageous manner, the electrically conducting material applied to the wall of the supply channel also forms, however, a hollow electrode which, in comparison to its dimensions in the surface plane of the substrate, has a relatively large area. The electrode manufactured according to the process therefore allows, in spite of a high locational resolution, a good electrical contact to a medium to be examined or treated.

The previously mentioned object can also be achieved in that the surface structure is manufactured from an electrically conducting material, in that in the area of the tip or edge at least one electrically conducting electrode layer is galvanized and/or applied by electrostatic powder coating onto this material, and in that a surface area of the substrate surrounding the electrode layer located on the tip or edge is then converted by a chemical reaction into an insulating layer or provided with such an insulating layer.

The invention makes use of the discovery that upon application of an electric voltage on the substrate or its surface structure in the area of the tip or edge, an especially high electrical field strength occurs. The electrode material to be galvanized or applied by electrostatic powder coating therefore preferably deposits in the area of the tip or edge of the substrate, while the remaining surface area of the substrate remains free of electrode material, so that the substrate material distinguished from the electrode material is arranged there. By a chemical treatment, the surface area that has the substrate material is converted into an insulating layer or provided with an insulating layer, whereby the electrode surface is then still electrically conducting only in the area of the electrode layer. For this purpose, the chemical treatment is selected such that the chemical reaction occurs only in the substrate material, while the electrode layer remains chemically unchanged to the greatest extent. Thus, in an advantageous way, the application of a lacquer mask surrounding the electrode layer can be omitted.

One embodiment of the process provides that the electrically conducting electrode layer is also applied onto the substrate outside of the area of the tip or edge, and thereafter, electrode material is stripped away from the surface of the electrode layer by etching, until the electrode layer is removed until a residual area remains in the area of the tip or edge. Possibly, electrode material applied to the substrate outside of the area of the tip or edge is thus removed by etching again from the surface of the substrate. On the tip of the edge, a residual area forming the electrode tip then remains, since the electrode layer is galvanized or coated with a greater thickness in the area of the tip of the edge due to the larger electric field strength there. The galvanizing or electrostatic coating of the electrode material can therefore be performed with a larger current strength and thus more quickly. The etching of the electrode material applied outside of the tip or edge area can be done, for example, in an etching bath or by vaporizing or spraying with an etching agent. However, a dry etching process, for example reactive ion etching, can also be applied.

It is especially advantageous if a material is selected for the electrode layer, which is more resistant to oxidation than the substrate material, and if the insulating layer is produced by oxidation of the surface area of the substrate surrounding the electrode layer. For this purpose, the substrate can, for example, be exposed to an oxygen-containing atmosphere under the action of heat. By the oxidation of the substrate, an electrically good insulating layer results on the surface of the substrate.

Another possibility consists in that for the electrode layer, a material is selected that is more resistant to nitration than the substrate material and in that the insulating layer is produced by nitration of the surface area of the substrate surrounding the electrode layer. The nitration can, for example, be performed using a heat treatment of the substrate in a nitrogen-containing atmosphere.

It is especially advantageous if the insulating layer is manufactured by anodic oxidization of the surface area of the substrate surrounding the electrode layer. To do this, for example, the area of the substrate having the electrode layer can be arranged in an electrolyte that etches the electrode layer in order to remove the electrode layer up to the residual area remaining in the area of the tip or edge. Then, the electrolyte for the anodic oxidation of the surface area of the substrate surrounding the remaining residual area of the electrode layer is exchanged with another anodic oxidizing electrolyte, and an electrical voltage is applied between the substrate and the electrolyte. As the electrolyte, for example, sulfuric acid, hydrogen peroxide, oxalic acid, or chromic acid can be used.

An advantageous embodiment of the process provides that when creating the surface structure, at least one electrically conducting coating is applied on the substrate, which is arranged on the surface of the surface structure. As substrate material, a good structurable material can then be used, which optionally can also be an insulator. The coating material is selected such that it is chemically well convertable into an electrical insulator. If the surface structure is applied to the substrate prior to the coating of the substrate, a material can even be used as a coating material which cannot be structured, or can only be poorly structured.

In an advantageous embodiment of the invention, it is provided that a supply channel is made in the substrate, which opens in close proximity to the tip or edge on the surface of the substrate, that the substrate is arranged in a first electrolyte at least with one area which has the tip or edge, and which does not have, or has only in small concentrations, ions of the galvanized electrode material, that through the supply channel a second electrolyte is supplied, which emerges at the tip or edge and which has the ions to be applied, and that for the galvanization of the electrode layer at the tip or edge, an electrical voltage is applied between the substrate and the second electrolyte. The electrolyte containing the ions of the electrode material to be galvanized is thus intentionally conducted through the supply channel to the surface area of the substrate which has the tip or edge, whereby a precipitation of electrode material on a surface area of the substrate located outside of that surface area is avoided. With an electrically conducting substrate, electrode material is precipitated, in addition to the area of the tip or edge, also on the wall of the supply channel, so that it forms an electrically conducting connection to the electrode tip or edge.

Preferably, the supply channel is made in such a manner in the substrate that its cross-section diminishes starting from the channel end facing away from the tip or edge to the opening arranged in the area of the tip or edge, and preferably this reduction is adjacent to the opening. The supply channel can thereby be manufactured better in production technology. For this purpose, the supply channel can optionally have arranged at the tip or edge in the area of its opening, a shoulder or a step which forms a transition from a channel section having larger cross-section to a channel section with a smaller cross-section having the opening. Through the locally expanded channel cross-section, in addition, possibly accruing reaction products can be better carried away during the application of the electrode layer.

In a preferred, advantageous embodiment of the invention, a semiconductor material can be used as the substrate. Optionally, in the manufacture of the electrode, measurement or evaluation electronics can then be directly integrated into the semiconductor material. As the semiconductor material, for example, silicon can be used, which can be provided with an electrically good insulating passivation layer through oxidation.

It is especially advantageous if in the area of the tip or edge, a noble metal is applied. The electrode tip or edge is then especially corrosion resistant and remains chemically neutral during chemical treatment for application of the insulating layer on the substrate material. Moreover, the electrode manufactured according to the process is better for the examination of chemically aggressive media, for example solutions containing salts. In comparison to processes in which at first, a noble metal layer is applied to the substrate over a large area, and then in the area of the tip or edge, a mask is applied in order to again remove the area of the noble metal layer located outside of the tip or edge area, the present process has the advantage that a contamination by the noble metal, of the production facilities used for the manufacture of the mask and etching, is avoided. Such a contamination of the manufacturing facilities is especially undesirable in electrodes, in whose substrate CMOS semiconductors are to be integrated in layers located below the electrode layer using mask technology, since the smallest impurities with a noble metal can readily impair the functionality of the CMOS semiconductors and, in particular, their gate oxides. Since the manufacturing facilities required for mask technology are costly and expensive, these same manufacturing facilities are used customarily for the manufacturing of the lower layers containing CMOS structural components, as they are for the layers near the surface. In the present process, on the other hand, for the application of the noble metal electrode layer by galvanic coating, electrostatic powder coating and/or radiation- based precipitation of an electrically conducting material from a chemical, separate manufacturing facilities can be used which can be prepared in a considerably more cost-effective manner.

The surface structure can thus be produced in that on the surface of the substrate, a recess is made in the electrically insulating material, that an electrically conducting material is brought into this recess, in particular a metal, that an area of the insulating material surrounding the conducting material is then removed by etching, until the conducting material forms a tip or edge projecting on the substrate surface, and that after that, on the tip or edge, at least one electrically conducting electrode layer is galvanized on and/or applied by electrostatic powder coating. It is thereby possible to manufacture the surface structure having the tip or edge by the exclusive use of manufacturing processes that are conventional in the manufacturing of CMOS-semiconductors. In an advantageous manner, most of the process steps provided for the manufacture of the surface structure can also simultaneously be used for the manufacture of conductor paths located in layers of a CMOS-semiconductor which are near the surface, so that they can be manufactured together with the surface structure in one work step. CMOS structural components can thus be integrated in a simple way into the substrate of the electrode. They can, for example, include part of a measuring amplifier or an evaluation device and/or a semiconductor switch, with which the active electrode area of the electrode located on the tip or edge can be connected to a voltage source.

It is especially advantageous, if after the application of the electrode layer, an area of the insulating material, which surrounds the conducting material and was brought into the recess, is again removed by etching, and if the surface area of the conducting material which is thereby uncovered is then converted by a chemical reaction into an insulating layer or is provided with an insulating layer. The electrically conducting electrode layer is then arranged at the free end of a projection that is electrically insulated on its surface at a distance from the surface of the substrate. In sum, a point electrode thus results, with which, for example, in a biological cell, the cell potential located in the interior of the cell can be measured through the cell membrane in a locationally resolved manner. For this purpose, the electrically insulated projection penetrates the cell membrane, and the electrode layer is arranged inside the cell insulated from the cell membrane.

One embodiment of the invention provides that the recess made in the substrate is completely filled with the electrically conducting material. An especially compact electrode projection thereby results.

In another embodiment, the recess made in the substrate is lined with the electrically conducting material, in particular by coating. It is thereby possible to construct the electrode as a hollow electrode.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

In a process for manufacturing an electrode indicated on the whole by 1, a three-dimensional surface structure is created on the surface of a substrate 2 using a structuring process, for example by anisotropic etching, by underetching of a lacquer layer or by vapor deposition of the substrate surface through an opening located in a mask arranged near the substrate surface.

Figure 1:
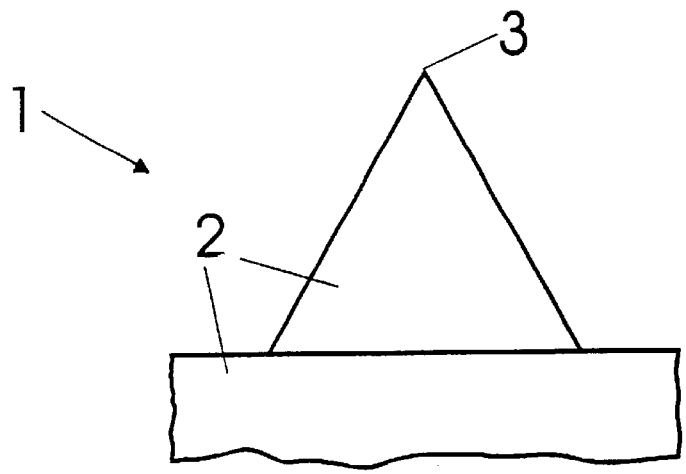
FIG. 1 is a side view of an electrically conducting substrate, which has a surface structure with a pyramid-shaped projection having a sharp tip.
Figure 2:
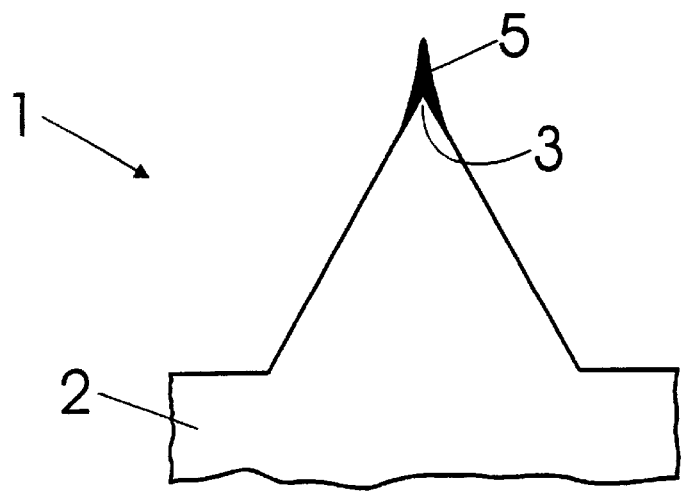
FIG. 2 is a cross-section through the arrangement shown in FIG. 1, after the galvanization of an electrode layer on the tip of the projection.

The surface structure can, for example, have a cone-shaped or pyramid-shaped projection, having on its furthest projecting free end area a sharp tip 3 or a sharp edge 4. In the process according to FIGS. 1 to 3, the substrate 2 consists of an electrically conducting material, for example silicon. The substrate 2 has the shape of a wafer, which has on its surface a plurality of tips 3, of which in FIGS. 1 to 3 for reasons of overview, only one is shown in each Figure.

Figure 7:
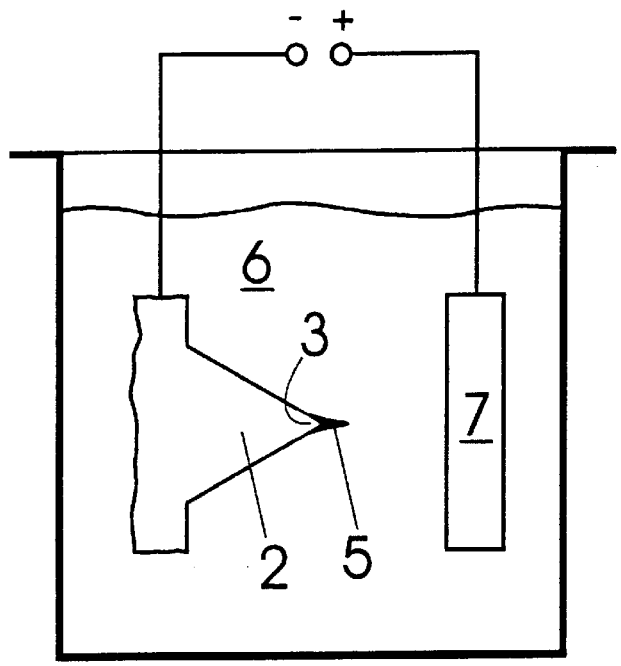
FIGS. 7 and 8 are cross-sections through a device for galvanizing a metallic electrode layer on the tip or edge area of the substrate.

On the tip 3 projecting on the surface of the substrate 2, a metallic electrode layer is galvanized. To do this, the substrate is immersed in an electrolyte 6 (FIG. 7), which contains ions of the metal to be galvanized on (plated). In the electrolyte 6 a sacrificial electrode 7 is additionally arranged, which has at least on its surface, the metal to be galvanized on. Here, the sacrificial electrode 7 is preferably positioned in such a manner in the electrolyte 6, that the tip 3 of the substrate 2 faces the sacrificial electrode 7. Then, the substrate 2 is connected to the minus pole and the sacrificial electrode 7 is connected to the plus pole of an electric voltage supply. An electric field thereby forms in the electrolyte 6, which has its greatest field strength in the area of the tip 3 of the substrate 2. In the electric field, the cations of the metal galvanized on, which are contained in the electrolyte, move onto the substrate 2 and preferably become deposited in the area of the tip 3 on the substrate 2, since there the electric field strength is the greatest. Here, the metallic electrode layer 5 forms in the area of the tip 3 (FIG. 2), while the remaining surface of the substrate 2 remains free of metallic material. A possible thin metallic layer that forms outside of the area of the tip 3 on the surface of the substrate 2 can optionally be removed using a subsequent etching process.

After the application of the electrode layer 5, the electrolyte 6 is exchanged for an electrolyte that is suitable for an anodic oxidation. In addition, the poles of the electric voltage supply are changed, i.e., the plus pole is connected to the substrate 2 located in the electrolyte 6 and the minus pole is connected to the sacrificial electrode 7. The substrate 2 is thereby anodically oxidized in the area of its surface that surrounds the electrode layer 5. On the surface of the substrate, an electrically good insulating oxide layer forms thereby, e.g., with a substrate 2 made of silicon, a silicon oxide, or with a substrate 2 made of aluminum, an aluminum oxide layer. The electrode layer 5 consists of a nobler material than the substrate 2, e.g., of a noble metal, and thus does not change during an anodic oxidation of the substrate 2. In sum, an electrode 1 results which is partially conducting in the area of the tip 3 and is electrically insulating in the surface area surrounding the electrode layer 5.

Figure 3:
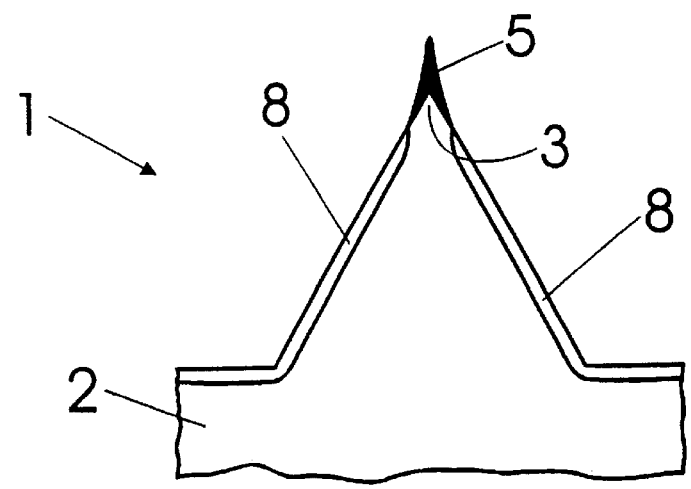
FIG. 3 is a cross-section through the electrode shown in FIG. 2, after the oxidation of an area of the substrate which is near the surface and surrounds the electrode layer.

As can be recognized in FIG. 3, the electrode layer 5 is connected to the electrically conducting substrate 2 so that, for example, a measurement signal incident on the electrode layer 5 can be measured in a simple way on the substrate 2. Correspondingly, a voltage can be supplied via the substrate 2 into the electrode layer 5. The electrode 1 can be used, for example, for the locationally resolved measurement on a cell culture deposited on the substrate 2.

Figure 4:
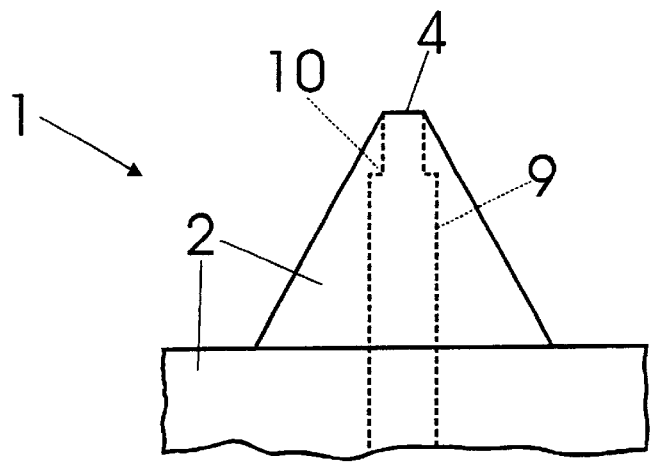
FIG. 4 is a representation similar to FIG. 1 wherein, however, a supply channel, depicted in dashed lines and having an opening surrounded by a sharp edge, was introduced into the substrate.
Figure 5:
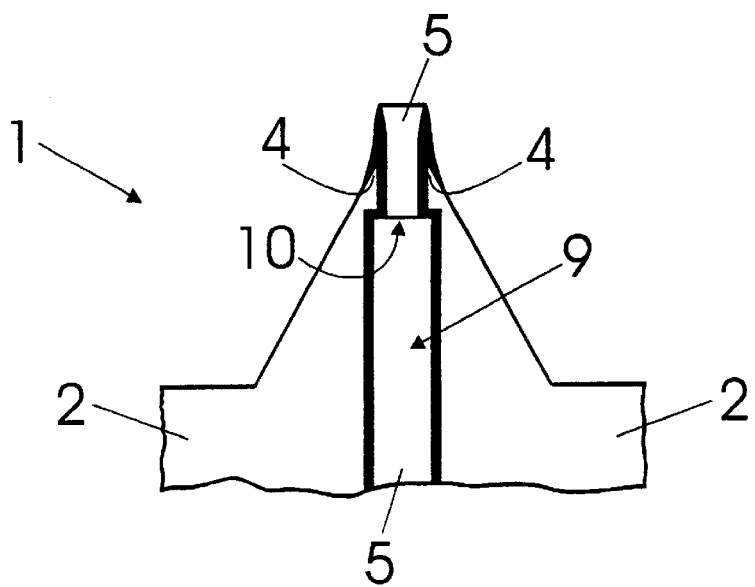
FIG. 5 is the substrate shown in FIG. 4, after the light-based application of an electrode layer on the edge of the projection.
Figure 6:
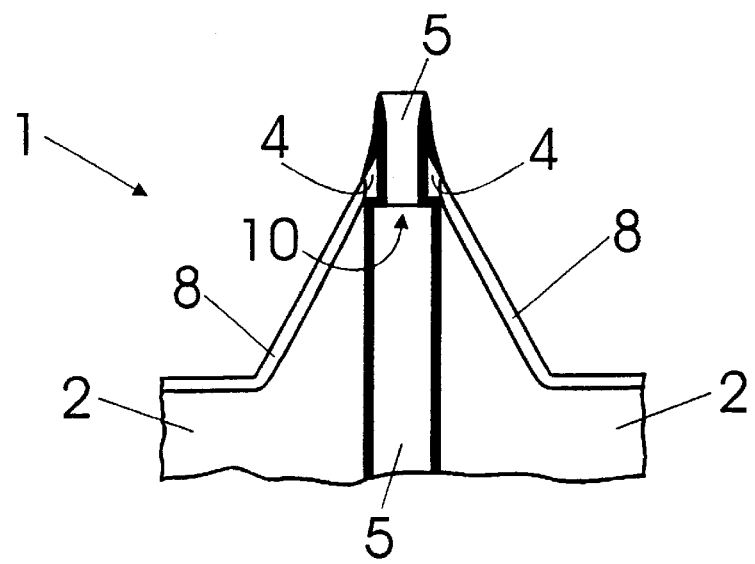
FIG. 6 is a cross-section through the electrode shown in FIG. 5, after the oxidation of the surface area of the substrate surrounding the electrode.

In the process according to FIGS. 4 to 6, a surface structure is created on the substrate 2 using a conventional structuring process. The surface structure has an approximately cone-shaped or pyramid-shaped projection. Next, from the rear side of the substrate 2 facing away from the projection (in FIG. 4 underneath), a supply channel 9 is made which leads to an opening located at the furthest projecting position of the projection. In the opening area the supply channel 9 is surrounded by a ring-shaped, sharp edge 4. As can be recognized especially well in FIG. 4, the supply channel 9 has a first channel section with a larger cross-section and a second channel section with a smaller cross-section, which forms the opening arranged on the edge 4. The two channel sections are connected together by a shoulder 10 arranged in proximity to the edge 4. By the varying cross-sections of the channel sections, the supply channel 9 can be manufactured better by fabrication technology. The supply channel 9 can be made by processes that are known per se, for example using laser drilling or trench etching into the substrate 2.

Through the supply channel 9 a chemical is supplied that exits at the edge 4 and deposits a metal upon being irradiated with electromagnetic radiation. During the supply of the chemical, laser radiation is coupled in at the end of the supply channel 9 facing away from the edge 4. The laser radiation passes through the supply channel 9 until reaching the edge 4. On the edge 4 and on the inner wall of the supply channel 9, metal is thus precipitated out of the chemical supplied through the supply channel 9. This metal deposits in the area of the edge 4 and on the inner wall of the supply channel 9 and forms the electrode layer 5 of a hollow electrode.

With an electrically conducting substrate 2 the surface area of the substrate 2 surrounding the electrode area located on the edge 4 is thereafter converted by a chemical reaction into an electrically insulating layer 8. This process step is omitted for a substrate 2 made of an electrically insulating material.

Figure 8:
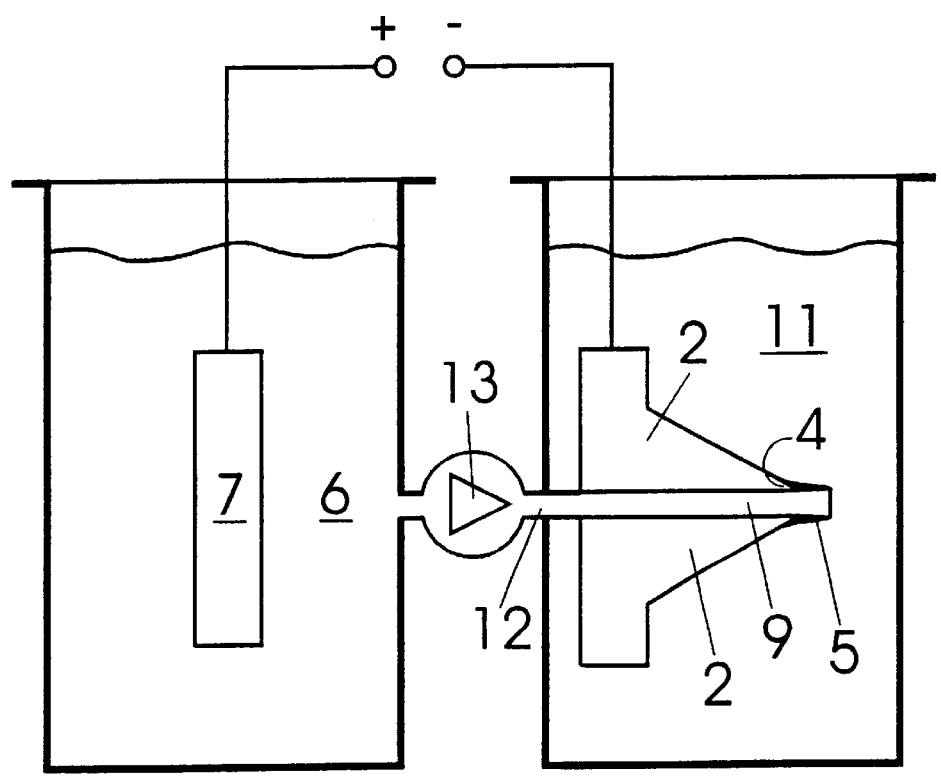

In a process according to FIG. 8, a substrate 2 is structured in the previously described manner and provided with a supply channel 9. The substrate 2 is then arranged in a first electrolyte 11, which does not have, or has only in small concentration, the ions of the metal galvanized on as the electrode. Through the supply channel 9 a second electrolyte is supplied, emerging at the edge 4 and having the ions to be applied. In FIG. 8 is clearly recognized that the end of the supply channel 9 facing away from the edge 4 is connected by a supply line to a supply container that has the electrolyte. In the supply line 12 a pump 13 is connected, which slowly pumps the electrolyte 6 through the supply channel 9 to the edge 4. As in the embodiment according to FIG. 7, the substrate 2 is connected to the minus pole and a sacrificial electrode 7 in contact with the electrolyte 6 is connected to the plus pole of a galvanizing voltage source. Metal is thereby galvanized (plated) onto the substrate 2 on the inner wall of the supply channel 9 and in the area of the edge 4. The volume flow of the pump 13 is selected such that the electrolyte emerging from the supply channel 9 on the edge 4 is essentially consumed, so that the metallic material is to be sure precipitated out in the area of the edge 4, but not on the cone-shaped or pyramid-shaped surface area of the substrate 2 connected to it. After the galvanization of the electrode layer, this area is anodically oxidized by reversing the poles of the galvanizing voltage source. An electrically insulating layer 8 thereby results on the surface of the substrate (FIG. 6).

Figure 9:
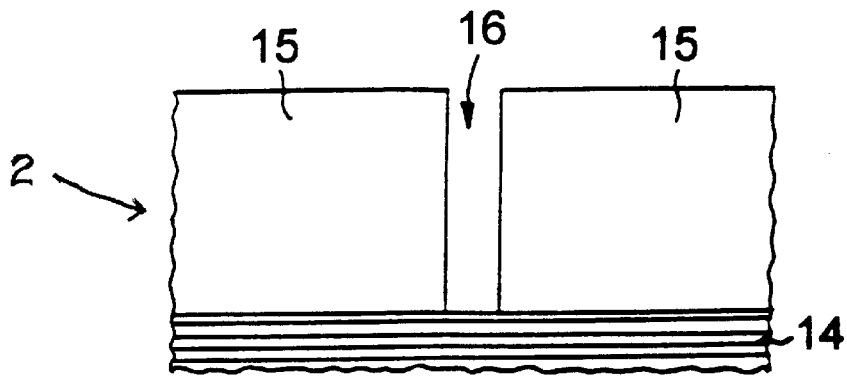
FIG. 9 is a cross-section through a substrate having an electrically insulating layer penetrated by a recess.
Figure 10:
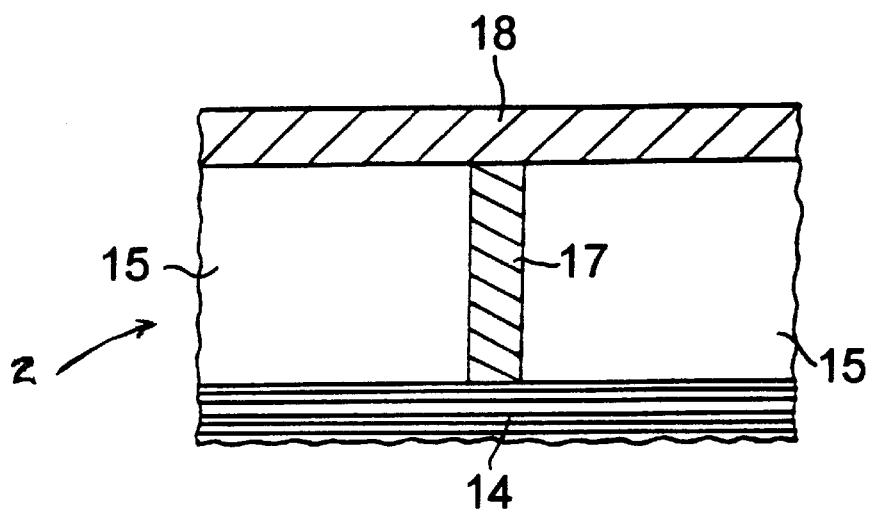
FIG. 10 is the substrate shown in FIG. 9, after an electrically conducting material was brought into the recess.
Figure 11:
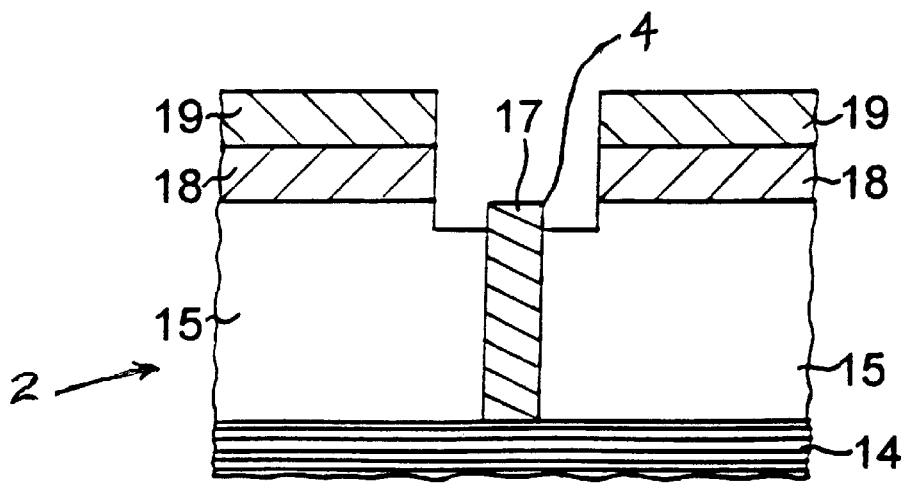
FIG. 11 is the substrate shown in FIG. 10, after the etching away of an area of the electrically insulating layer surrounding the conducting material.

In the embodiment shown in FIGS. 9 to 13, a layer made of electrically insulating material 15 is applied onto an electrically conducting substrate layer 14. Then, a recess 16 is made into this material 15 from the surface of the substrate 2, which penetrates the insulating material 15 up to the electrically conducting substrate layer 14 (FIG. 9). An electrically conducting material 17, for example tungsten or aluminum, is introduced into the recess 16 using a known process. As can be recognized well from FIG. 10, the electrically conducting material 17 forms a through column in the insulating material 15.

Next, a passivation layer 18 is applied on the substrate 2. The passivation layer 18 covers the electrically insulating material 15 and the electrically conducting material 17 located in the recess 16. Then, a photomask 19 that is chemically resistant to an etching agent is applied on the passivation layer. The photomask 19 has a gap in the area of the electrically conducting material 17. Then, an area of the passivation layer 18 located behind the gap in the photomask 19 and an area of the insulating material 15 located behind the passivation layer and surrounding the electrically conducting material 17 are removed by etching. As can be recognized especially well from FIG. 11, the electrically conducting material 17 forms an edge 4, which projects out on the surface of the substrate 2.

Figure 12:
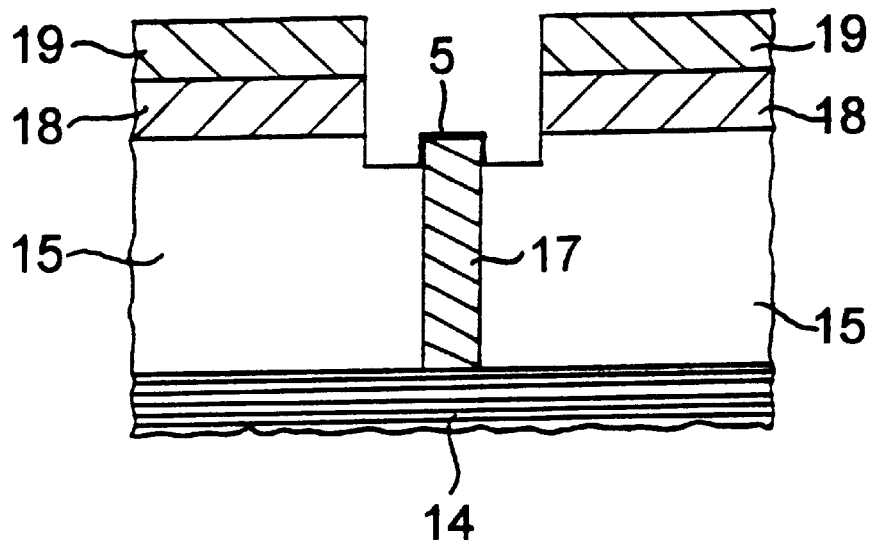
FIG. 12 is the substrate shown in FIG. 11, after the galvanization of an electrode layer on the tip of the electrically conducting material.
Figure 13:
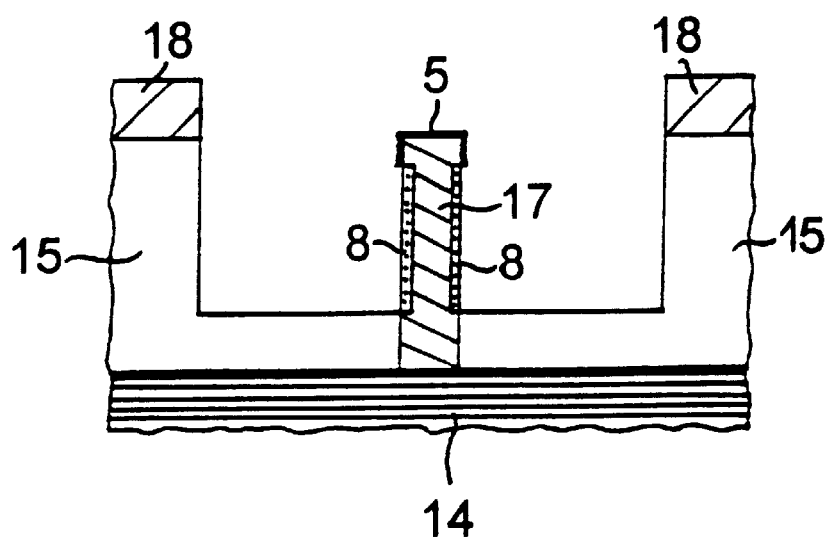
FIG. 13 is the substrate shown in FIG. 12, after the anodic oxidation of a surface area of the conducting material which is connected to the electrode layer.

Next in the area of the edge 4, an electrically conducting electrode layer 5 made of a noble metal, for example gold or platinum, is galvanized on (FIG. 12). Then, an additional area of the electrically insulating material 15 between the galvanized electrode layer 5 and the substrate layer 14 is removed by etching. In this process, the same photomask 19 is used as in the previous etching process. The surface area of the conducting material 17 which is laid bare by this additional etching process is converted by anodic oxidation into an insulating layer 8. In addition, the photomask 19 is removed (FIG. 13).

In sum, an electrode 1 thus results, having an electrically insulated projection on its surface, which carries the electrode layer 5 on its free end. Here, the electrode layer 5 is connected via the electrically conducting material 17 to the likewise electrically conducting substrate layer 14. Via this layer, for example, an electric voltage can be applied to the electrode layer 5 or a measurement signal can be taken on the electrode layer 5.

It should also be mentioned that the electrically insulating material 15 also can have several layers running essentially parallel to the substrate surface, which are locally removed in order to lay bare the electrically conducting material 17 in one or more etching steps performed one after the other. In this way, the open lengths of the electrode projection can be enlarged.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

I claim:

1. A process for manufacturing an electrode (1) comprising creating a surface structure having at least one tip (3) or edge (4) on a substrate (2), forming a supply channel (9) in the substrate (2), such that the supply channel opens in close proximity to the tip (3) or edge (4) on a surface of the substrate, supplying a chemical through the supply channel (9), such that the chemical emerges at the tip (3) or edge (4), the chemical being one which upon irradiation with electromagnetic and/or particle radiation precipitates out an electrically conducting material, and irradiating the chemical in an area of the tip (3) or edge (4) with electromagnetic and/or particle radiation to precipitate out the electrically conducting material at the tip (3) or edge (4).

2. The process according to claim 1, wherein the electromagnetic and/or particle radiation is beamed through the supply channel (9) into the area of the tip (3) or edge (4).

3. A process for manufacturing an electrode (1) comprising creating a surface structure having at least one tip (3) or edge (4) on a substrate, wherein the surface structure is produced from an electrically conducting material, wherein in the area of the tip (3) or edge (4) at least one electrically conducting electrode layer (5) is galvanized and/or applied by electrostatic powder coating thereon, and wherein a surface area of the substrate (2) surrounding the electrode layer (5) located on the tip (3) or edge (4) is converted by a chemical reaction into an insulating layer (8) or provided with such an insulating layer.

4. The process according to claim 3, wherein for the electrode layer (5) a material is selected which is more resistant to oxidation than a material of the substrate, and wherein the insulating layer (8) is produced by oxidation of a surface area of the substrate (2) surrounding the electrode layer (5).

5. The process according to claim 3, wherein for the electrode layer (5) a material is selected which is more resistant to nitration than a material of the substrate, and wherein the insulating layer (8) is produced by nitration of a surface area of the substrate (2) surrounding the electrode layer (5).

6. The process according to claim 3, wherein the insulating layer (8) is produced by anodic oxidation of a surface area of the substrate (2) surrounding the electrode layer (5).

7. The process according to claim 1, wherein when creating the surface structure, at least one electrically conducting coating is applied on the substrate (2), which is arranged on the surface of the surface structure.

8. The process according to claim 1, wherein the substrate (2) is arranged in a first electrolyte (11) at least with one area which has the tip (3) or edge (4), and which does not have, or has only in small concentrations, ions of a galvanized electrode material (5), wherein through the supply channel (9), a second electrolyte (6) is supplied, which emerges at the tip (3) or edge (4) and which has the ions to be applied, and wherein for galvanization of the electrode layer (5) at the tip (3) or edge (4), an electrical voltage is applied between the substrate (2) and the second electrolyte (6).

9. The process according to claim 1, wherein the supply channel (9) is formed in such a manner in the substrate (2) that its cross-section becomes reduced starting from the channel end facing away from the tip (3) or edge (4) to the opening arranged in the area of the tip (3) or edge (4).

10. The process according to claim 1, wherein a semiconductor material is used as the substrate (2).

11. The process according to claim 1, wherein in the area of the tip (3) or edge (4) a noble metal is applied.

12. The process according to claim 1, wherein a recess is made in the electrically insulating material, wherein an electrically conducting material is introduced into the recess, wherein an area of the insulating material surrounding the conducting material is removed by etching until the conducting material forms a tip (3) or edge (4) projecting on the substrate surface, and wherein on the tip (3) or edge (4) at least one electrically conducting electrode layer (5) is galvanized on and/or applied by electrostatic powder coating.

13. The process according to claim 12, wherein after application of the electrode layer (5), an area of the insulating material, which surrounds the conducting material and was introduced into the recess, is again removed and wherein the surface area of the conducting material which is laid bare by the removal is then converted by a chemical reaction into an insulating layer (8) or is provided with an insulating layer (8).

14. The process according to claim 12, wherein the recess made in the substrate (2) is completely filled with the electrically conducting material.

15. The process according to claim 12, wherein the recess made in the substrate (2) is lined with the electrically conducting material.

16. The process according to claim 1, wherein the electrically conducting material comprises a metal.

17. A process for manufacturing an electrode (1) comprising creating a surface structure having at least one tip (3) or edge (4) on a substrate, wherein the surface structure is produced from an electrically conducting material, applying at least one electrically conducting electrode layer (5) in the area of the tip (3) or edge (4) and also onto the substrate outside of the area of the tip (3) or edge (4) by galvanizing and/or applying an electrostatic powder coating thereon, and thereafter removing a portion of the electrically conducting material from the electrode layer (5) by etching until the electrode layer (5) is removed up to a residual area remaining in the area of the tip (3) or edge (4).

* * * * *